United States Patent
Taylor et al.

(10) Patent No.: US 6,614,873 B1
(45) Date of Patent: Sep. 2, 2003

(54) INTERACTIVE DITIGAL RADIOGRAPHIC SYSTEM

(75) Inventors: Robert Montgomery Taylor, Bear, DE (US); Kelly Sue Herbst, Bear, DE (US)

(73) Assignee: Direct Radiography Corp., Newark, DE (US)

( * ) Notice: Subject to any disclaimer, the term of this patent is extended or adjusted under 35 U.S.C. 154(b) by 0 days.

(21) Appl. No.: 09/831,696

(22) PCT Filed: Nov. 12, 1999

(86) PCT No.: PCT/US99/26702

§ 371 (c)(1),
(2), (4) Date: May 11, 2001

(87) PCT Pub. No.: WO00/31522

PCT Pub. Date: Jun. 2, 2000

Related U.S. Application Data

(60) Provisional application No. 60/109,209, filed on Nov. 20, 1998.

(51) Int. Cl.⁷ .............................................. G01N 23/04
(52) U.S. Cl. ........................................ 378/62; 378/98
(58) Field of Search ............................ 378/62, 63, 98, 378/114, 115, 116

(56) References Cited

U.S. PATENT DOCUMENTS

| | | | |
|---|---|---|---|
| 4,255,662 A | 3/1981 | Waterkamp | 250/416 |
| 4,773,086 A | 9/1988 | Fujita et al. | 378/4 |
| 5,254,480 A | 10/1993 | Tran | 437/2 |
| 5,315,101 A | 5/1994 | Hughes et al. | 250/208.1 |
| 5,319,206 A | 6/1994 | Lee et al. | 250/370.09 |
| 5,563,421 A | 10/1996 | Lee et al. | 250/580 |
| 5,648,660 A | 7/1997 | Lee et al. | 250/370.09 |
| 5,768,336 A | 6/1998 | Khutoryansky et al. | 378/116 |
| 5,773,832 A | 6/1998 | Sayed et al. | 250/370.09 |
| 5,804,832 A | 9/1998 | Crowell et al. | 250/580 |

*Primary Examiner*—David V. Bruce
(74) *Attorney, Agent, or Firm*—RatnerPrestia

(57) ABSTRACT

The present invention provides an interactive integrated medical radiographic system comprising in combination a radiation source, an electronic detector including an analog to digital converter, a central control device including a CPU and a user interface a memory and a display device. The radiation source emits on command a radiation beam that is directed to pass through a target and impinge on the electronic radiation detector. The central control device communicates with both the memory, the radiation source, and the electronic detector, and is programmed to interact with an operator through the user interface and in response to input by the operator, and data stored in the memory, to initialize the detector, to set the radiation source for a desired exam, to retrieve from memory a sequence of steps representing actions by the operator required to perform said desired exam, and to sequentially guide the operator through said sequence of actions.

21 Claims, 2 Drawing Sheets

INTERACTIVE DITIGAL RADIOGRAPHIC SYSTEM

This application claims the benefit of Provisional application Ser. No. 60/109,209, filed Nov. 20, 1998.

BACKGROUND OF THE INVENTION

1. Field of the Invention

This invention relates to radiographic systems and more particularly to an interactive digital radiographic system which controls both the radiation source, and the radiation detector, and guides an operator through the necessary steps to complete a requested examination

2. Description of Related Art

Radiographic examinations entail obtaining at least one and often multiple radiograms of a patient. To obtain such radiograms it is necessary to have a radiation source such as an X-ray machine, and a radiation detector such as radiation sensitive film or other radiation detector. The radiation is imagewise modulated as it passes through an object having varying radiation absorption areas.

In the past decade there has been great progress made in the area of direct radiographic imaging using electronic detectors comprising a two dimensional array of minute sensors to capture a radiation generated image. Information representing an image is captured, often as a charge distribution stored in a plurality of charge storage capacitors in individual sensors arrayed in a two dimensional matrix. We will refer to such detectors generically as electronic detectors to differentiate them from the traditional radiography detectors which employ a photosensitive film usually in combination with an intensifying screen to produce a photographic image of the incident X-ray radiation.

The electronic detectors typically comprise a two dimensional array of sensors with associated switching and addressing circuitry built on an insulating substrate, usually a glass plate. U.S. Pat. No. 5,319,206 issued to Lee et al. on Jun. 7, 1997, shows a typical direct radiation detector comprising an array of sensors for the generation and capture of charges following exposure to X-ray radiation. Readout of the stored charges is accomplished in any one of a plurality of manners. U.S. Pat. No. 5,648,660 issued to Lee et al. discloses a method for the readout of stored charges in a electronic imaging panel.

The availability of a radiogram in electronic signal format, permits the use of digital signal conversion and all the advantages of signal storing, retrieval and processing associated with digital imaging.

At many medical institutes a radiographic examination procedure begins with a Doctor requesting from the department of Radiology to obtain one, or a series of radiograms, of a patient. The request form typically includes the following information:

(a) Patient demographic data, such as social security, patient I.D. name, data of birth, address, insurance etc.

(b) Examination requester information, such as name of Doctor requesting examination and his department.

(c) Examination procedure such as modality (X-ray, Cat Scan, etc.) region (Chest, extremities, etc.) and procedure (frontal, lateral, number of views, placement of patient, etc.).

In a typical Hospital today, the doctors no longer request specific views and exposures for each patient, but simply identify specific examinations by a name or code. The actual exposure procedures corresponding to these examinations are predetermined and the radiology technician simply follows these predetermined procedures once he receives the examination request code.

With the availability of digitized images, picture archiving and communication systems (known as PACS) have been developed which store, communicate and display images and other data on demand at various locations. In a typical PACS application the system stores image data sent from x-ray, CT, MRI and other imaging systems in a database, and transfers requested image data from the database to an image workstation. The image workstation displays received image data on a cathode ray tube (CRT) display for study by the doctor, who, following his study of the image may prepare a report and attach the report to the image for future reference when the image or report are needed again. The image workstation may also display the image as a hard copy printed locally by a local printer connected to the PAGS system.

Yet, in spite of the availability of direct radiation capturing devices and PACS systems, there has not been developed as yet a system which integrates a number of distinct functions of individual modalities, output devices, and existing systems into an integrated interactive radiographic imaging system able to provide faster access to better diagnostic images and to greatly reduce the possibility of operator error.

SUMMARY OF THE INVENTION

It is an object of this invention to provide such an integrated system which offers the advantages of complete radiation exposure control, image capture, storage and display combined with interactive operator guidance through the examination specific steps in combination with the use of predetermined default settings automatically recalled, to complete a requested procedure.

It is thus the object of the present invention to provide an interactive integrated medical radiographic system comprising in combination:

a radiation source;

an electronic detector including an analog to digital converter;

a central control device including a CPU and a user interface; and a memory.

More particularly, the radiation source emits on command a radiation beam that is directed to pass through a target and impinge on the electronic radiation detector. Still according to this invention, the central control device is in communication with both the memory, the radiation source, and the electronic detector.

The central control device is programmed to interact with an operator through the user interface and in response to input by the operator through the user interface, and data stored in the memory, to initialize said imaging detector, to set said radiation source for a desired exam, to retrieve from memory a sequence of steps representing actions by the operator required to perform said desired exam, and to sequentially guide the operator through said sequence of actions.

The radiographic system typically will also include a display device on which the central control may display, after appropriate formatting, an image captured by the electronic detector following exposure of a target to imaging radiation. The central control may be further programmed to retrieve from the memory an Exam Specific Algorithm (ESA) and to apply this algorithm to the exposure data representing the radiogram prior to displaying it.

The ESA may be applied as a default image correction or may be selected by the operator from a plurality of ESAs stored in memory through the user interface.

In displaying a radiogram on a selected output display device, the central control may further include an interactive link between said control and the display device whereby the control identifies the display and formats the data for display in a format acceptable by the display device.

The central control may be further programmed to accept alpha-numeric input data representing demographic patient and exam data, to store the data, and to associate the data with a particular radiogram.

It is also an object of this invention to provide a program embodied in a machine readable medium for programming a control computer to control a radiation source to emit a radiation beam directed to pass through a target and to impinge on an electronic detector. The machine readable program instructs the computer to perform the following steps in response to information and commands entered by an operator through a computer user interface, and from data stored in a memory and retrieved therefrom:

i) to initialize the imaging detector and the radiation source;

ii) through the user interface, to guide the operator through a sequence of actions needed to expose to the radiation beam a target, typically a patient; and iii) to retrieve and store the exposure data in the memory.

The machine readable program further includes instructions for the computer to prompt the operator to evaluate and to accept and reject exposure data from the detector prior to storing the exposure data. The exposure data represents a radiogram of the target.

In addition, the machine readable program further includes instructions for the computer to apply selected image processing algorithms to the exposure data and to format and transmit the exposure data for display on a display device after it has interrogated the display device about display format requirements and having formatted the exposure data in a format acceptable to the display device.

BRIEF DESCRIPTION OF THE DRAWINGS

The invention can be more fully understood from the following description thereof in connection with the accompanying drawings described as follows.

DESCRIPTION OF THE PREFERRED EMBODIMENT(S)

Figure 1:
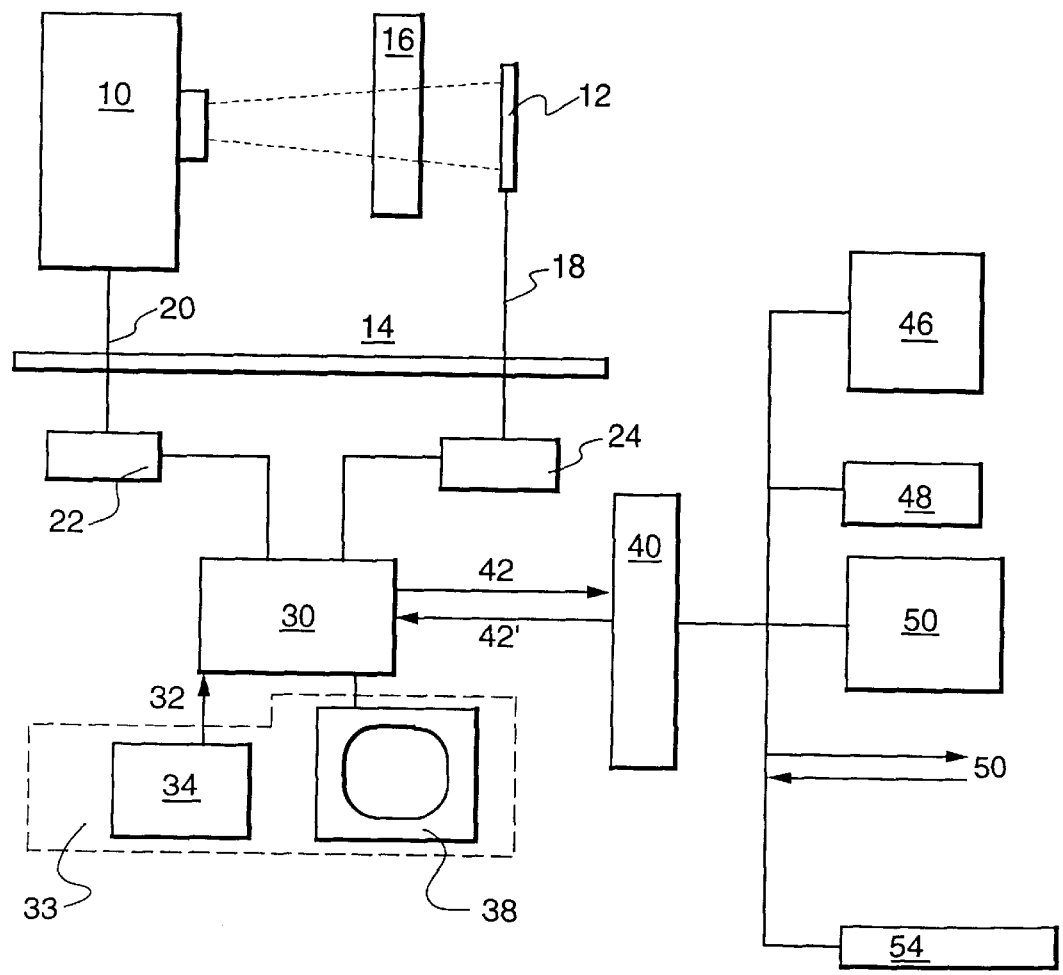
FIG. 1 shows an interactive radiographic examination system in accordance with this invention.

Throughout the following detailed description, similar reference characters refer to similar elements in all figures of the drawings.

Referring now to FIG. 1, there is shown a radiographic system in accordance with the present invention.

The system comprises a radiation source 10 (exposure unit) and an electronic detector 12 in an examination room 14. Typically a target 16 which in medical diagnostic applications is usually a patient, is placed between the detector 12 and the radiation source 10 and the exposing radiation is transmitted through the target and impinges onto the detector.

The detector 12 can be any radiographic detector capable of generating an electrical signal representing impinging radiation intensity variations. Such radiographic detectors are described inter alia in U.S. Pat. No. 5,773,832, issued Jun. 30, 1998 to Sayed et al., U.S. Pat. No. 5,254,480, issued Oct. 19, 1993 to Nang T. Tran, or U.S. Pat. No. 5,315,101, issued May 24, 1994 to Hughes et al.

A preferred detector contemplated for use in the present invention is a direct conversion radiation detector of the type disclosed in the aforementioned U.S. Pat. No. 5,648,660 issued to Lee et al. Such specific detector is used to facilitate an understanding of this invention and is not intended to limit the invention to this specific embodiment.

As disclosed in this patent the detector comprises a two dimensional array of individual radiation sensors on a supporting dielectric base forming a panel of appropriate size, usually 14 by 17 inches. The panel is enclosed in an enclosure such as disclosed in U.S. Pat. No. 5,804,832 issued to Crowell et al. The sensors each comprise a charge storage capacitor and a switching transistor adjacent the capacitor. A photoconductive layer is placed over the individual sensors and a biasing electrode is placed over the photoconductive layer. Charge blocking layers are placed on one or both sides of the photoconductive layer. In one embodiment an insulating layer is used between the capacitor and the photoconductive layer. Upon exposure to radiation electron and hole pairs are freed in the photoconductive layer. Under an imposed static magnetic field, electrons migrate to the biasing electrode and holes to the charge storage capacitor (depending on the polarity of the applied field).

Following exposure the biasing field is removed and the accumulated charge in the individual sensors is read out, amplified, digitized and stored. The panel is next reconditioned for the next exposure, by exposing to illuminating radiation as disclosed in U.S. Pat. No. 5,563,421 issued to Lee et al. Preferably between exposures the radiation detection panel is continuously cycled between a state where the biasing voltage is zero and a state where a biasing voltage other than zero is applied to the biasing electrode followed by image readout even when no exposure has occurred. This is referred to as the standby state, as distinguished from the ready state in which the cycling has been interrupted and a proper biasing voltage has been applied to the sensors.

The biasing, cycling, readying and readout of the detector is controlled by a detector controller 24 connected to the detector 12 through a cable 18.

The radiation source is any commercial X-ray unit. For this description, the X-ray unit is made by Fisher Imaging Corporation for use in hospital radiation departments as an exposure source for radiographic imaging. Typically such X-ray units also include a controller 22 which controls the radiation intensity and duration based on selections made by the operator. The controller 22 is shown here connected to the X-ray unit through a cable 20. The controllers may be within or without the examination room and may be integral or separate with the source or the detector.

According to the present invention there is shown connected to both the X-ray controller 22 and the detector controller 24 over lines 26 and 28 respectively, a central control unit 30.

While the functions of the central control may be implemented in whole or in part in hardware, central control 30 typically comprises a computer (or a combination of computers) and includes a CPU (central processing unit) and the required interfaces to interface with the X-ray controller 22 and detector controller 24. When the central control is a computer the computer is programmed to perform the required functions using a program storage device readable by the computer which tangibly embodies the set of instructions comprising the program to perform the various control functions in the order required. The program storage device may be in the form of hard disk drive, floppy disk, tape, CD-ROM, programmable chips, or combinations of the above. Typically, the central control output is a stream of electrical signals, preferably digital signals, even though, depending on the requirements of the device receiving the output, the signals may also be analog or both. The latter is particularly true where the central control directly commands electromechanical devices such as motors or relays.

Associated with the central control is a user interface 33. The user interface is used to communicate with the central control device and includes a typical communication means, such as a keyboard, a mouse, a bar code reader or a combination of the above shown collectively as block 34 and may also include a disk drive, either floppy or CD-ROM or both. Typically the user interface will also include a display device 38 including a display screen which is preferably styled as a "windows" screen. By this it is meant that the screen presents a number of icons selectable by a pointer operated by a mouse or keyboard keys. Selection of an icon may represent a command to the central control to perform a corresponding function (i.e. save data, select a specific ESA and apply to exposure data, etc.) or may open a "window" providing the operator with additional selection of commands, such as a plurality of stored ESAs from which the operator may select a preferred one, or a default ESA for the specific exam which the operator may accept. The display screen may also be used by the central control to prompt the operator to perform certain actions as required by a specific exam.

There is also stored in the memory at least one set of procedure steps corresponding to a desired examination. The control device upon selection of an examination through the user interface, retrieves these procedure steps and based on the retrieved procedure steps, controls the operating parameters of the radiation source, and the radiation detector. At the same time, through the user interface, it guides the operator through the necessary actions to complete the examination, by displaying on the user interface information related to the current status of the procedure and to the remaining actions required to complete the selected procedure.

The central control 30 is usually, even though this is not essential for the operation of the present system, connected to other hospital devices through an interface 40 over lines 42 and 42'. This interface 40 permits the central control to communicate with other devices such as a central databank 46, a printer or camera 48, and a soft diagnostic display 50, such as a high resolution CRT. In addition, the interface permits connecting the central control to other multi-device systems via a network connection 52, such as the LINX® system, provided by Sterling Diagnostic Imaging, a division of AGFA Corporation, which permits the connection of different diagnostic modalities to different display devices, all being located at different places in a hospital.

Both the radiation source and the radiation detector have been shown with their own electronic controllers. Alternatively, the functions of detector controller 24 and radiation controller 22 may be incorporated into the central control 30 through appropriate programming and interfacing, particularly where a system such as described is integrally designed, rather than being assembled from different components manufactured by different sources. The other hospital device interfaces are also preferably an integral part of the programmed central control, however, as illustrated, such an interface may also be a stand alone element.

The same is true regarding the connectivity functions of a data transmission system such as the previously mentioned LINX system. Finally either directly or through a system such as the LINX system, remote input of information and access to the central control 30 may be available through a remote input 54. This remote input may, for example, be used by the admitting division to enter alphanumeric data representing patient demographic information, or by an examining physician to order a specific examination for a specific patient.

The databank 46 may be used to store not only demographic patient information, but patient images (radiograms) and reports of prior examinations. These may be used by the doctor in comparative studies to compare a current image with a prior one of the same patient.

The central control 30 memory preferably includes a number of ESA (exam specific algorithms) and any required constants which are used in displaying a radiogram. The use of such algorithms is described in co-pending PCT application US98/03249 filed Feb. 20, 1998. As disclosed in the aforementioned application the algorithms serve to map the linear data obtained from the detector to the gray scale transfer function of the display medium in a way that the information displayed resembles in appearance a traditional photographic radiogram but one that contains an enhanced version of the original data so that only the pertinent portion of the data for a specific examination is displayed. Typically the result of this mapping operation is the creation of a calculated LUT (Look Up Table) associated with the particular radiogram which is applied to the original data prior to displaying the data. The function of applying the ESA LUT may be performed by the central controller 30 or by the output device. This LUT may be stored with the image data in the image data bank 46 for later retrieval.

Figure 2:
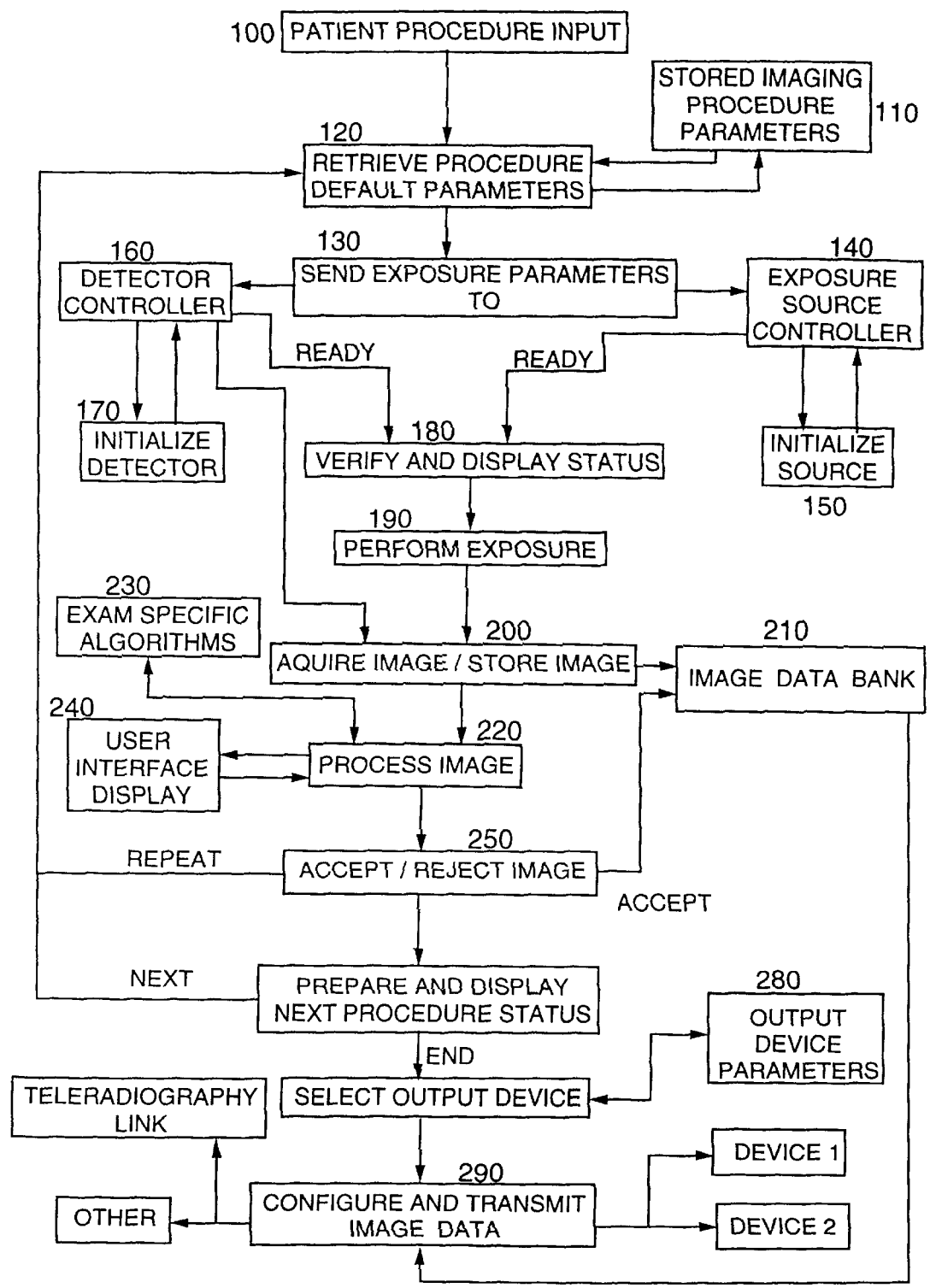
FIG. 2 shows a flow diagram of the steps performed by the system in implementing the present invention.

FIG. 2 shows a flow diagram of the sequence of operations performed by the controller 28 according to the present invention. The flow diagram may be used to develop specific software to program specific controllers to perform the required functions for this system.

An initial first step not illustrated, consists of loading in the system the necessary information for the system to operate. This information, as a minimum, will include the required steps to perform a number of typical exams. Each examination may be identified by a code or may be spelled out, or both, so that the required steps to perform an exam can be later retrieved automatically by the controller.

An x-ray examination typically consists of one or more radiographic views of the target. For example, a chest examination may require four exposures, i.e. chest lateral left side, chest lateral right side, chest frontal, and chest back for one exam, and only two views for another, i.e. Chest frontal and lateral right side. For each such exposure, there are provided default image acquisition parameters, and possibly fill in data that must be supplied by the operator, such as patient weight. There is thus a series of steps associated with each exposure and a series of exposures associated with each exam. The central control 30 performs all required steps for each exposure in the proper sequence, prompting the operator along the way to act (i.e. initiate radiation exposure, place patient in proper position etc.) or to input the required information such as patient size, and provides default system settings for each for each exposure.

The process of loading the exam steps and default parameters for various exams is typically done at the time of installation of the system. However, additional exams may be loaded at later times as they are developed.

The first step by the operator is the selection of particular exam. In a typical hospital situation a patient arrives at the radiography department accompanied by a physician's usually coded request for a particular exam. The operator requests the exam procedure through the user interface (block 100). In a typical embodiment, the available exams stored in the system are displayed on the operator interface display for selection. However a particular exam may also be picked automatically based on input information received from the site's central computer information systems, or by the central processor user interface reading a bar code which may be imprinted on the physician's request sent to the operator.

The technology for creating and activating selection windows, and for selecting subroutines to perform predetermined functions with the use of a mouse is well known technology and requires no further explanation in this invention.

Once the operator selects an exam from the selection of preloaded exams in the system, the controller retrieves from memory (110) the corresponding sequence of steps required to perform the selected exam, (120) as well as all other parameters required by the selected exam, such as initialization parameters of the source for each exposure, including radiation intensity and exposure duration as well as initialization of the electronic detector. Once the default parameters are retrieved they are sent (130) to the exposure source controller (140) and the source is initialized (150). Similarly the detector controller (160) receives initialization parameters and switches the detector (170) from standby to ready. When both source and detector are "ready" the central control displays the ready status to the operator and either automatically or upon further command by the operator performs the exposure (190).

Following exposure the image is acquired from the detector via the detector controller. The acquired image has preferably undergone initial image processing for bad pixel correction, gain control, noise reduction, etc. This data is stored (200) in the memory representing the image data bank memory (210).

The acquired and stored image next, preferably, undergoes further image processing (220) at which time, exam specific algorithms are applied to it (230). These algorithms may be applied automatically, as default algorithms corresponding to the exam procedure selected, or may be selected by an operator for the particular exposure. The result is displayed in the user interface display (240). The operator is asked to accept or reject the image (250). If accepted both the raw image, and the applied algorithm are stored in the data bank (210). If rejected the raw data is discarded, and the exposure of the target repeated.

Once accepted and the image stored, the system retrieves the parameters for the next exposure and indicates its status to the operator (260). The process is repeated till all required exposures for a particular examination have been accepted and stored.

Display of the results may follow immediately after each exposure or may be by retrieving and configuring the data at a later time. In either case the operator selects an output device and/or location (270) whereupon the controller identifies the output device parameters needed, and configures the data for the selected device, i.e. device 1, device 2, teleradiography, other, . . . and transmits the properly formatted data to the device for display.

The central control 30, therefore, according to the present invention, upon receipt of a command to begin the exposure, automatically prepares both the detector and the exposure source. This process may require multiple steps, which may be different depending on the detector used. With the electronic detector used in describing this invention, these steps will include switching the detector from a standby mode to the ready state preparing it for exposure; it will also include initializing the exposure unit to emit the proper radiation intensity for the proper time period. The initialization process may also include actuating an anti-scatter grid, if one is needed for the particular exposure, and, possibly, actuating and positioning radiation field limiting baffles. Thus synchronization of the actual radiation emission and image capture by the detector requires that the central control assures that all requisite elements of the exposure be in the proper state before the actual radiation exposure occurs.

The user interface displays to the operator the current status of the examination. This display may take the form of showing miniature figures representing the sequence of exposure views to be taken, with the first exposure view highlighted; and the system condition status, such as wait, ready for exposure, next etc. The operator will act in response to the user interface prompts and status report, issuing commands to the central control or changing the target orientation to obtain another view, as required by the particular exam sequence.

Once the controller has retrieved the specific exam procedure and prompted the operator to initiate an exposure, the operator issues the exposure command. The central control 30 sends the exposure parameters to the source and the electronic detector controllers, if these are separate from the central control, or to the sections of the central control that perform these function when integral with the central control. When initialization of both source and detector is completed, the user interface may indicate to the operator that he may proceed with the actual exposure, requiring an additional action by the operator, such as activation of an exposure switch, or may proceed to the actual exposure without further input from the operator. In either case the user interface indicates to the operator when the exposure has been completed.

The preferred embodiment uses miniature figurines to indicate the status of each exposure view required by a particular exam. The figurines portray a stylized patient position that should be used before each view is shot and provide an indication "thumbnail" of the actual shot that was taken once the exposure acquisition is complete. The operator will check patient placement to see if the patient is in the proper position for the exposure (i.e. chest lateral). This may be done by checking that the miniature figurine position corresponds to the patient position, before issuing the exposure command.

The display indicates to the operator when the exposure has been completed. Following completion of the radiation exposure the central control acquires the image data from the detector. This image data undergoes two stages of image processing. The first stage is detector dependent and involves pixel equalization, bad pixel correction, noise reduction, prior exposure artifact elimination and any other required image processing that is normally independent of the type of image captured but is related to the detector used to capture the image. The result of this image correction produces a raw image set of pixels which are typically stored in the memory. This memory may be a single large memory integral with the central control or, as is most often the case, a separate memory for general data storage accessible by the central control.

The next level of image processing is exam related. It has been observed that certain gray scale modifications to the data may be used to enhance the appearance for particular diagnostic purposes of the radiographic data represented the raw image data. Based on the type of radiogram, i.e. chest posterior/anterior, chest lateral etc., the central control automatically retrieves from a data bank a set of exam specific algorithms (E SA) and associated constants which have been predetermined to produce an optimum image for this type radiogram, and generates a LUT to be used with the raw image pixel data in the display of the radiogram.

Alternatively, the ESA algorithms may be applied by the detector controller to generate the requisite LUT, rather than through the central control, and the image processing also done by the detector controller. The actual point of application of the image correction is not essential to the practice of this invention.

Optionally, the system may provide for operator modification of the ESA LUT generated based on the system defaults. This modification can be stored with the raw image data and retrieved by the operator for future use. A low resolution default image representing a preview of the complete radiogram is next displayed using the selected LUT for review by the operator. If the image is acceptable to the operator he indicates the acceptance through the input interface, and the image data and LUT are saved in an image database for display of the full radiogram.

If the image is not acceptable, i.e. the patient has moved or was improperly positioned etc., the operator rejects the image and the same exposure is repeated.

Once an image has been accepted, the central control updates the status display showing the next procedure step required, preferably by intensifying the next miniature figure showing to the operator the next patient positioning requirement, and resetting the system by sending the new set of parameters to the detector and to the x-ray exposure unit, and repeating the sequence of steps previously described.

Display of the captured radiograms for diagnostic purposes may be done in any one of a plurality of output devices. Typical output devices are a high resolution CRT (soft display) or a hard copy printer (hard display) such as a laser printer exposing photosensitive material, a thermal printer, an ink jet printer etc.

These devices may be located near the central control 30 or may be remote therefrom. There may also be a number of different type of hard output display devices made by different manufacturers having different display capabilities and requiring different data formatting.

The operator will usually know which display device has been requested for a particular examination and will have entered this information in the central control at the time he entered the examination request. Based on this input the central control will next select the output device and properly configure both the device and the data for display. This configuring may include proper driver selection from a stored bank of required drivers, initializing the device to accept data, and formatting the data for display, i.e. size, orientation, multiple images in a single sheet, etc. The control device will also apply the LUT associated with the image data to the image data prior to display, or, depending on the output device capabilities, the central control may provide the LUT to the device together with the data and the output device may apply the LUT to the data prior to display.

Display may be done as soon as the data has been received from the detector controller and the ESA applied to develop the display LUT, that is almost instantaneously following the exposure, or the data may be stored in an image database with the derived LUT for subsequent retrieval and display. The display may be done in a remote output device or in a display device connected to the detector and its controller.

Preferably, demographic patient information is also stored and, if desired, displayed with the image data, thereby forming a database which includes all needed information about a patient, with numerous radiograms which may be taken at different times and which may be displayed side by side to determine any changes in the radiograms.

The systems interface 40 may be used to transmit the image data, LUT, and patient information to a remote location for display or storage either through a hard wired local area network such as the LINX system mentioned earlier, or to a remote location which may be a part of a wide area network over telephone lines using a modem.

The ability of this system to interface with a local (or wide) area network offers a number of advantages over prior stand alone radiation exposure units with independently controlled radiation detectors. The data entry discussed earlier may also be accomplished in a single step from a single interface station, or it may be accomplished at different times from remote and proximate locations. For instance, upon admission, a patient demographic data is obtained by the admitting personnel in a hospital, including insurance information for future billing. This information may be stored in the same patient database as the radiogram image data and LUT will be stored. The doctor's examination request may be also entered by the doctor from his office and attached to the patient demographic information. When the patient arrives at the X-ray unit station, upon entering the patients name the full information is retrieved and the proper procedure selected without further input by the operator reducing the chance of a wrong examination being performed.

Following completion of the examination, the required billing information may be attached to the patient data and retrieved by or sent to the Hospital accounting department system at a later date, again without requiring double entry.

While the present system has been described with reference to certain specific equipment and devices, this was done to facilitate an understanding of the invention rather than to limit the invention. As mentioned earlier the detector used may be any one of a number of different type of direct radiographic detectors capable of providing an electrical signal representing an image which signal may be digitized. In the description reference is often made to separate controllers however the functions of the various controllers may be incorporated in a single computer having sufficient computing capacity to accept and implement the necessary programming software to combine the different functions of the different individual controllers. Similarly there is mention to various memory banks, such as a data bank for image storage, a data bank for patient information, a data bank for storage of ESAs, etc. As the practitioner will surely realize, this is again a matter of choice and a single databank can be used whenever desirable.

These and similar modifications are to be construed as being encompassed within the scope of the present invention as set forth in the appended claims wherein we claim:

1. An interactive integrated medical radiographic system comprising in combination:
   a radiation source;
   an electronic imaging radiation detector including an analog to digital converter;
   a central control device including a CPU and a user interface; and a memory,
wherein
(a) said radiation source emits on command a radiation beam;
(b) said beam is directed to pass through a target and impinge on said electronic; imaging radiation detector, and
(c) wherein said central control device is in communication with both the memory, the radiation source, and the imaging radiation detector;
the improvement wherein comprises:
the central control device is programmed to interact with an operator through the user interface and in response to input by the operator through the user interface, and data stored in the memory, to initialize said imaging detector, to set said radiation source for a desired exam, to retrieve from memory a sequence of steps representing actions by the operator required to perform said desired exam, and to sequentially guide the operator through said sequence of actions.

2. The system according to claim 1 wherein the central control device is further programmed to retrieve exposure data from said detector representing a radiogram of the target.

3. The system according to claim 2 wherein one of the actions performed by the operator is to evaluate said radiogram and to accept and reject said radiogram, the central control being further programmed to store said exposure data representing said accepted radiogram in the memory.

4. The system according to claim 1 further comprising a display device.

5. The radiographic system according to claim 4 wherein the central control is further programmed to retrieve from the memory an Exam Specific Algorithm (ESA) and apply said ESA to said exposure data prior to displaying said exposure data.

6. The radiographic system according to claim 5 wherein said ESA is selected by the operator through the user interface.

7. The radiographic system according to claim 4 wherein the programming of the central control to display said data on a display device includes an interactive link between said control and the display device whereby the control identifies the display and formats the data for display in a format acceptable by the display device.

8. The radiographic system according to claim 7 wherein the central control is programmed to perform image rotation.

9. The radiographic system according to claim 1 wherein said exam steps include prompting the operator to obtain a number of sequential radiation exposures of said target in accordance with said desired exam.

10. The radiographic system according to claim 1 wherein the central control is further programmed to accept alpha-numeric input data, to store said data, and to associate said data with said exposure data.

11. The radiographic system according to claim 10 wherein said target is a patient, said exposure data represents a medical diagnostic radiogram and said alpha-numeric data is demographic patient and exam data.

12. The radiographic system according to claim 10 wherein the central control is further programmed to display said alpha-numeric data on the display system together with said exposure data.

13. The radiographic system according to claim 1 wherein said input through said user interface comprises a bar code.

14. The radiographic system according to claim 1 wherein said user interface comprises a mouse and a display screen, said mouse operating a pointer on said display screen and said display screen comprises windows containing input commands to the central control activated through said pointer.

15. The radiographic system according to claim 1 wherein said detector and said radiation source also include control electronics, and wherein said central controller interfaces with said control electronics.

16. A program embodied in a machine readable medium for programming a control computer to control a radiation source to emit a radiation beam directed to pass through a target and to impinge on an electronic imaging radiation detector including an analog to digital converter, also controlled by said computer, said machine readable program for instructing said computer to perform the following steps in response to information and commands entered by an operator through a computer user interface, and from data stored in a memory and retrieved therefrom:
i) initialize said imaging detector and said radiation source;
ii) through the user interface guide the operator through a sequence of actions needed to expose to said radiation beam a target; and
iii) to retrieve and store said exposure data in the memory.

17. The program according to claim 16 wherein said machine readable program further includes instructions for said computer to prompt the operator to evaluate and to accept and reject exposure data from said detector prior to storing said exposure data the data representing a radiogram of the target.

18. The program according to claim 16 wherein said machine readable program further includes instructions for said computer to:
apply selected image processing algorithms to said exposure data; and
to format and transmit said exposure data for display on a display device.

19. The program according to claim 16 wherein in step (i) the step of guiding the operator through the user interface includes guiding the operator to expose to said radiation beam said target a number of times according to a preset procedure identifying for the operator a number of desired views of said target.

20. The program according to claim 16 wherein said machine readable program further includes instructions for said computer to interrogate said display device about display format requirements and to format said exposure data in a format acceptable to said display device prior to transmitting said exposure data for display on said display device.

21. The program according to claim 20 wherein said machine readable program further includes instructions for said computer to rotate said exposure data prior to transmitting said data for display on said display device.

* * * * *